US012628730B2

(12) United States Patent
Faers et al.

(10) Patent No.: US 12,628,730 B2
(45) Date of Patent: May 19, 2026

(54) METHOD, VEHICLE AND SYSTEM FOR WEED CONTROL MANAGEMENT

(71) Applicant: BAYER AKTIENGESELLSCHAFT, Leverkusen (DE)

(72) Inventors: Malcolm Faers, Düsseldorf (DE); Andrew Charles Chapple, Langenfeld (DE)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 655 days.

(21) Appl. No.: 17/913,415

(22) PCT Filed: Mar. 15, 2021

(86) PCT No.: PCT/EP2021/056465
§ 371 (c)(1),
(2) Date: Sep. 21, 2022

(87) PCT Pub. No.: WO2021/190966
PCT Pub. Date: Sep. 30, 2021

(65) Prior Publication Data
US 2023/0136009 A1     May 4, 2023

(30) Foreign Application Priority Data

Mar. 23, 2020    (EP) .................................... 20164973

(51) Int. Cl.
*A01C 14/00*        (2006.01)
*A01B 69/00*        (2006.01)
(Continued)

(52) U.S. Cl.
CPC .............. *A01C 14/00* (2013.01); *A01B 69/00* (2013.01); *A01M 7/00* (2013.01); *A01M 21/00* (2013.01);
(Continued)

(58) Field of Classification Search
CPC ..... A01B 69/00; A01B 69/001; A01B 69/007; A01B 69/008; A01B 79/00; A01B 79/005;
(Continued)

(56) References Cited

U.S. PATENT DOCUMENTS 7,194,965 B2 * 3/2007 Hickey ................ A01B 79/005
                                                                            111/900
9,213,905 B2 * 12/2015 Lange .................... G06V 20/58
(Continued)

FOREIGN PATENT DOCUMENTS

WO       WO-0195164 A1 * 12/2001    .......... A01B 79/005
WO       WO-2023230730 A1 * 12/2023    .......... A01M 7/0089

OTHER PUBLICATIONS

Andújar, D. et al. Discriminating Crop, Weeds and Soil Surface with a Terrestrial LIDAR Sensor. Sensors, vol. 13, No. 11, Oct. 29, 2013, pp. 14662-14678 [online], [retrieved on Dec. 16, 2025]. Retrieved from the Internet <https://pmc.ncbi.nlm.nih.gov/articles/PMC3871132/pdf/sensors-13-14662.pdf> (Year: 2013).*
(Continued)

*Primary Examiner* — John E Breene
*Assistant Examiner* — Daniel M Quinn
(74) *Attorney, Agent, or Firm* — Harness, Dickey & Pierce, P.L.C.

(57)                    ABSTRACT

The present invention relates to a method (10) to control weeds comprising the steps of: a) acquiring geopositional information of planted crop seeds on an agricultural field and generating a crop seed map, b) acquiring soil elevation data and the corresponding geopositional information of the soil elevation on the agricultural field where the crop seeds have been planted or are being planted at at least two different time points and generating soil surface profile maps of the agricultural field, the soil surface profile maps show-
(Continued)

ing the soil surface profiles at the at least two different time points, c) comparing the soil surface profile maps and the crop seed map to identify differences in the soil elevation profile that are not associated with seed growth of the planted seeds on the agricultural field, d) generating a weed control agent spray map on the basis of the differences in the identified soil elevations on the agricultural field that are not associated with seed growth of the planted crop seeds on the agricultural field.

8 Claims, 5 Drawing Sheets

(51) Int. Cl.

| | |
|---|---|
| *A01M 7/00* | (2006.01) |
| *A01M 21/00* | (2006.01) |
| *A01M 21/04* | (2006.01) |
| *B64D 1/18* | (2006.01) |
| *B64U 101/32* | (2023.01) |
| *B64U 101/45* | (2023.01) |
| *G01C 15/00* | (2006.01) |
| *G01C 21/00* | (2006.01) |
| *G01C 21/04* | (2006.01) |
| *G01C 22/00* | (2006.01) |
| *G01N 33/00* | (2006.01) |
| *G01S 7/40* | (2006.01) |
| *G01S 13/00* | (2006.01) |
| *G01S 17/00* | (2020.01) |
| *G05D 1/00* | (2024.01) |
| *G06F 16/00* | (2019.01) |
| *G06F 16/20* | (2019.01) |
| *G06Q 50/02* | (2024.01) |
| *A01B 79/00* | (2006.01) |
| *B64U 101/30* | (2023.01) |
| *B64U 101/40* | (2023.01) |
| *G01S 13/06* | (2006.01) |
| *G01S 13/46* | (2006.01) |
| *G01S 17/88* | (2006.01) |
| *G01S 17/89* | (2020.01) |
| *G05D 1/242* | (2024.01) |
| *G05D 1/243* | (2024.01) |
| *G05D 1/246* | (2024.01) |
| *G05D 1/692* | (2024.01) |
| *G05D 1/698* | (2024.01) |
| *G05D 107/20* | (2024.01) |
| *G05D 109/10* | (2024.01) |
| *G05D 111/00* | (2024.01) |
| *G05D 111/10* | (2024.01) |
| *G06F 16/29* | (2019.01) |

(52) U.S. Cl.
CPC ............. *A01M 21/043* (2013.01); *B64D 1/18* (2013.01); *G01N 33/00* (2013.01); *G01S 7/4034* (2021.05); *G01S 13/00* (2013.01); *G01S 17/00* (2013.01); *G06F 16/00* (2019.01); *G06Q 50/02* (2013.01); *A01B 79/005* (2013.01); *A01M 7/0089* (2013.01); *B64U 2101/30* (2023.01); *B64U 2101/32* (2023.01); *B64U 2101/40* (2023.01); *B64U 2101/45* (2023.01); *B64U 2201/10* (2023.01); *B64U 2201/104* (2023.01); *G01C 15/00* (2013.01); *G01C 21/005* (2013.01); *G01C 21/04* (2013.01); *G01C 21/38* (2020.08); *G01C 21/3804* (2020.08); *G01C 21/3811* (2020.08); *G01C 21/3826* (2020.08); *G01C 21/3867*

(2020.08); *G01C 21/3881* (2020.08); *G01C 21/3885* (2020.08); *G01C 22/00* (2013.01); *G01S 13/06* (2013.01); *G01S 13/46* (2013.01); *G01S 17/88* (2013.01); *G01S 17/89* (2013.01); *G05D 1/00* (2013.01); *G05D 1/242* (2024.01); *G05D 1/243* (2024.01); *G05D 1/246* (2024.01); *G05D 1/692* (2024.01); *G05D 1/6987* (2024.01); *G05D 2107/21* (2024.01); *G05D 2109/10* (2024.01); *G05D 2111/00* (2024.01); *G05D 2111/10* (2024.01); *G06F 16/20* (2019.01); *G06F 16/29* (2019.01)

(58) Field of Classification Search
CPC .......... A01C 7/00; A01C 14/00; A01C 21/00; A01M 7/00; A01M 7/0089; A01M 7/0092; A01M 21/00; A01M 21/043; B64B 1/24; B64D 1/18; B64D 1/24; B64D 27/026; B64D 31/06; B64D 1/25; G01C 15/00; G01C 21/005; G01C 21/04; G01C 21/38; G01C 21/3804; G01C 21/3811; G01C 21/3826; G01C 21/3867; G01C 21/3881; G01C 21/3885; G01C 22/00; G01N 33/00; G01N 33/0098; G01S 7/4034; G01S 13/00; G01S 13/06; G01S 13/46; G01S 17/00; G01S 17/88; G01S 17/89; G05D 1/00; G05D 1/0088; G05D 1/0212; G05D 1/0287; G05D 1/227; G05D 1/242; G05D 1/243; G05D 1/246; G05D 1/646; G05D 1/6482; G05D 1/6987; G05D 2107/21; G05D 2109/10; G05D 2109/18; G05D 2111/10; G05D 2111/17; G05D 1/692; G05D 2111/00; G06F 16/00; G06F 16/20; G06F 16/29; G06Q 50/00; G06Q 50/02; B64U 2101/40; B64U 2101/45; B64U 2201/10; B64U 80/86; B64U 2101/30; B64U 2101/32; B64U 2201/104
USPC ................................ 33/320; 47/1.7; 382/154
See application file for complete search history.

(56) References Cited

U.S. PATENT DOCUMENTS

| | | | | |
|---|---|---|---|---|
| 9,265,187 | B2 * | 2/2016 | Cavender-Bares ...... | A01C 7/00 |
| 10,721,306 | B2 * | 7/2020 | McClelland ............ | H04L 67/12 |
| 10,881,095 | B2 * | 1/2021 | Boyd .................. | A01M 7/0089 |
| 10,882,065 | B2 * | 1/2021 | Davis ................... | A01B 69/001 |
| 11,001,380 | B2 * | 5/2021 | Nahuel-Andrejuk ........................ | |
| | | | | G05D 1/101 |
| 11,059,582 | B2 * | 7/2021 | Nahuel-Andrejuk ........................ | |
| | | | | B64U 10/14 |
| 11,771,077 | B2 * | 10/2023 | Fu ....................... | A01M 7/0089 |
| | | | | 47/1.7 |
| 11,957,072 | B2 * | 4/2024 | Blank ...................... | A01C 5/08 |
| 2001/0016788 | A1 * | 8/2001 | Hauwiller ............ | A01B 79/005 |
| | | | | 700/283 |
| 2003/0036852 | A1 * | 2/2003 | Ell ......................... | A01C 21/00 |
| | | | | 702/5 |
| 2012/0101861 | A1 * | 4/2012 | Lindores .............. | A01B 79/005 |
| | | | | 705/7.11 |
| 2012/0237083 | A1 * | 9/2012 | Lange .................... | G06F 16/29 |
| | | | | 382/103 |
| 2014/0012732 | A1 * | 1/2014 | Lindores .............. | A01B 79/005 |
| | | | | 705/37 |
| 2014/0076216 | A1 | 3/2014 | Kormann et al. | |
| 2015/0187109 | A1 * | 7/2015 | Mentzer .................. | G06T 11/00 |
| | | | | 345/632 |
| 2016/0302351 | A1 * | 10/2016 | Schildroth ............. | H04L 67/12 |
| 2017/0131718 | A1 * | 5/2017 | Matsumura ............ | H04N 23/11 |
| 2018/0075545 | A1 * | 3/2018 | Richt ................... | G06V 20/188 |

(56)  References Cited

U.S. PATENT DOCUMENTS

| | | | | |
|---|---|---|---|---|
| 2018/0129210 | A1* | 5/2018 | Achtelik | G05D 1/0094 |
| 2018/0263171 | A1* | 9/2018 | Rupp | G06N 7/06 |
| 2018/0271027 | A1* | 9/2018 | Funabashi | A01B 79/005 |
| 2018/0364157 | A1* | 12/2018 | Ghiraldi | A01C 21/007 |
| 2019/0009905 | A1* | 1/2019 | Kaechi | G06Q 50/02 |
| 2019/0104722 | A1* | 4/2019 | Slaughter | A01M 7/0089 |
| 2019/0150357 | A1* | 5/2019 | Wu | H04N 7/188 |
| 2020/0037598 | A1* | 2/2020 | Wonderlich | A01C 7/105 |
| 2020/0072809 | A1* | 3/2020 | Bhanu | G01N 29/036 |
| 2021/0097632 | A1* | 4/2021 | Xu | G06Q 50/02 |
| 2021/0186005 | A1* | 6/2021 | Sibley | G05D 1/0274 |
| 2021/0204467 | A1* | 7/2021 | Van De Woestyne | A01C 21/007 |
| 2021/0342956 | A1* | 11/2021 | Ethington | G06Q 10/06375 |
| 2022/0078964 | A1* | 3/2022 | Takeda | A01G 25/02 |
| 2022/0132828 | A1* | 5/2022 | Kwak | G06T 7/0004 701/50 |
| 2022/0317702 | A1* | 10/2022 | Chowdhary | G05D 1/243 |
| 2022/0340278 | A1* | 10/2022 | Faers | B60V 1/08 |
| 2023/0028706 | A1* | 1/2023 | Watson | G06Q 10/04 |
| 2023/0112376 | A1* | 4/2023 | Strnad | G06V 20/188 47/1.7 |
| 2023/0135631 | A1* | 5/2023 | Faers | B64U 80/30 701/3 |
| 2023/0343090 | A1* | 10/2023 | Khait | G06V 20/188 |
| 2023/0406502 | A1* | 12/2023 | Faers | A01M 7/0042 |

OTHER PUBLICATIONS

[item U continued] <DOI: 10.3390/s13111466> (Year: 2013).*
Aamir et al., "An Optimized Architecture of Image Classification Using Convolutional Neural Network",1 Journal of Image, Graphics and Signal Processing, Oct. 8, 2019, 10 pages.

* cited by examiner

Soil Elevation Profile Map / at Time Point 1 a)

Soil Elevation Profile Map / at Time Point 2 b)

d)

Crop Seed Map/ c)

■ Geoposition of a crop seed

▨ Geoposition of an emerging weed/of emerging weeds

▨ Geoposition of soil elevation changes due to other issues such as weather incidents e)

▨ Areas which need to be sprayed with a weed control agent

Soil that is pushed up by the weed germination activity

Weed
shoot

Each represent schematic soil elevation
patterns that emerge due weed germination
activities

METHOD, VEHICLE AND SYSTEM FOR WEED CONTROL MANAGEMENT

CROSS-REFERENCE TO RELATED APPLICATIONS

This application is a U.S. national stage filing under 35 U.S.C. § 371 of International Application No. PCT/EP2021/056465, filed on Mar. 15, 2021, which claims the benefit of, and priority to, European Patent Application No. 20164973.8, filed on Mar. 23, 2020. The entire disclosure of each of the above applications is incorporated herein by reference.

FIELD OF THE INVENTION

The present invention relates to a method for weed control management, to vehicle(s) for weed control management, to a system for weed control management, as well as to a computer program product.

BACKGROUND OF THE INVENTION

The general background of this invention is weed control and in particular pre-emergence weed control. Modern agriculture faces many challenges in producing sufficient food in a safe and sustainable way. One of the challenges that affect the quality and quantity of agricultural produce comes from unwanted weeds, which can have significant negative impacts on the yield and quality of agricultural produce. Solutions to this include spraying agricultural fields with chemical and biological herbicidal products, both prior to the emergence of weeds and after their emergence. However, these approaches have the disadvantage that relatively high amounts of products are applied and not always at the optimum time or place. A highly efficient treatment is at the pre-emergence stage but after germination when the first roots are developing. Herbicidal products that inhibit the growth of roots are very effective at this stage where the roots are not sufficiently developed to overcome the inhibition effect of the herbicidal products. However, as the location of the weeds is not known at the pre-emergence stage herbicidal products are applied on the whole field and not only where weeds are growing.

SUMMARY OF THE INVENTION

It would be advantageous to have improved means for weed control management (and in particular for pre-emergence weed control management) in order to apply chemical and biological herbicidal products more specifically to agricultural fields. The object of the present invention is solved with the subject matter of the independent claims, wherein further embodiments are incorporated in the dependent claims. It should be noted that the following described aspects and examples of the invention apply also for the method for weed control, the vehicle(s) for weed control, the system for weed control, and for the computer program product.

According to a first aspect, there is provided a method to control weeds comprising the steps of:
- a) acquiring geopositional information of planted crop seeds on an agricultural field and generating a crop seed map,
- b) acquiring soil elevation data and the corresponding geopositional information of the soil elevation on the agricultural field where the crop seeds have been planted or are being planted at at least two different time points and generating soil surface profile maps of the agricultural field, the soil surface profile maps showing the soil surface profiles at the at least two different time points,
- c) comparing the soil surface profile maps and the seed map to identify differences in the soil elevation profile that are not associated with seed growth of the planted seeds on the agricultural field,
- d) generating a weed control agent spray map on the basis of the differences in the identified soil elevations on the agricultural field that are not associated with seed growth of the planted crop seeds on the agricultural field.

Thus, the geolocation of the crop seeds in the soil on the agricultural field is recorded during planting. The crop seed map refers to a two-dimensional or three-dimensional display of the crop seed geopositional distribution on an agricultural field after planting. The soil elevation profile of the agricultural field is measured e.g. shortly after planting of the crop seeds and later—at a second time point—when weeds have begun to germinate but not yet emerged or just emerged. By data comparison, the differences in the soil elevation profiles at two different time points indicate where weeds potentially grow. Before weeds emerge, the soil is displaced as the growing shoot pushes upwards. This soil displacement can be detected by appropriate sensors. Machine learning algorithms support the discrimination of soil displacements due to reasons not associated with the weed germination such as for example soil displacements due to weather incidents, soil erosions, bird and animal marks etc. As it is decisive that the emerging crop seeds are not sprayed and as the soil displacement caused by weeds and crops can be similar it is necessary to identify the geolocation of the crop seeds during planting and to consider the geolocation of the crop seeds when generating a weed control agent spray map. The weed control agent spray map refers to (at least a) two-dimensional (or three-dimensional) display of weed (germination and emergence) geopositional distribution on an agricultural field where a weed control agent can be applied to appropriately control the weeds on the field. In this manner, weeds can be identified at a very early point in time which allows precision farming weed control applications at the pre-emergence phase.

In an example, the data for the crop seed map and the soil surface profile map showing the soil surface profile at the first time point are acquired on the agricultural field with an agricultural vehicle at the same time.

In other words, the data for the crop seed map and the soil surface profile data for a first time point are acquired in one operational process. E.g. a seed planter vehicle is planting crop seeds on an agricultural field. The geolocation of the crop seed is recorded during the planting process. E.g. with a seed metering system with a sensor that senses a passing seed, a timer to timestamp when a seed passes the sensor; all synchronized with a GPS system of the seed planter vehicle. At the same time a sensor on the seed planter vehicle can acquire data in regard to the soil elevation profile at a first point in time. These combined operational processes have the advantage that no additional ground vehicle operation is necessary for acquiring the necessary data on the agricultural field with benefits in regard to $CO_2$ emissions and avoidance of soil compaction damage.

In an example, the method comprises and additional step e), wherein a weed control agent is applied to the agricultural field according to the weed control agent spray map.

In other words, the weed control agent spray map can be used by a vehicle to apply a herbicide in a precision farming approach at a very early weed growth stage. This has the advantage that not only less herbicide is sprayed due to the precision application approach but that also less herbicide is necessary because the weeds at an earlier growth stage are easier to control than at a later stage.

In an example, the steps a) to e) of the method are performed prior to the emergence and/or during the emergence of a plurality of shoots of the crop seeds and/or weeds on the agricultural field.

Thus, the method of weed control management is in particular useful at an early growth stage after crop seeds have been planted when competition for nutritional resources between the crop seed plants and weeds is high.

In an example, the geopositional information of the planted crop seeds on the agricultural field is acquired by at least one sensor that is configured to record geopositional information of the crop seeds impinging on the soil during planting of the crop seeds.

Thus, various known detection techniques can be used to acquire information about the geolocation of the seeds on the agricultural fields. As described above, a metering system with a sensor that senses a passing seed, a timer to timestamp when a seed passes the sensor, in synchronization with GPS system can be used to assess the geoposition of crop seeds on the agricultural field. Alternative techniques include for example image analysis of images acquired with a camera from seeds impinging on the soil during the planting process together with GPS data.

In an example, the soil elevation data and the corresponding geopositional information of the soil elevation on the agricultural field is acquired with a sensor that is configured to generate pulses of light towards the soil surface and to measure the time for any reflections and location determining means.

In this manner, known sensors such as a lidar sensor (also known as LIDAR and LiDAR) with high resolution in combination with a GPS system can be used to acquire the soil elevation data.

According to a second aspect of the invention, there is provided a vehicle for weed control management comprising a plurality of sensors comprising at least one seed position sensor and at least one soil elevation sensor, a control and processing unit, and a seed planting unit. The vehicle is configured to plant crop seeds on an agricultural field with the seed planting unit. The at least one seed position sensor is configured to collect seed geoposition data of the crop seeds impinging on the soil surface from the seed planting unit during planting. The control and processing unit is configured to receive the seed geoposition data from the at least one seed position sensor to generate a crop seed map of the agricultural field. The at least one soil elevation sensor of the vehicle is configured to collect soil elevation data, the soil elevation data comprising elevations amounts and the corresponding geopositional information of the soil elevations on the agricultural field. The control and processing unit is configured to receive the soil elevation data from the at least one soil elevation sensor to generate a soil surface profile map of the agricultural field, wherein the soil surface profile map shows the soil surface profile at a first time point. The seed position data and the soil elevation data are acquired at the same instance when the plant crop seeds are planted on an agricultural field with the seed planting unit of the vehicle.

In other words, the vehicle for weed control management can be a seed planter vehicle with appropriate sensor equipment to measure the geolocation of the crop seeds on the soil as well as the surface structure (with high resolution) of the agricultural field shortly after the planting process (e.g. after the wheels of the seed planter vehicle have passed). In this manner, useful data for weed control management can be obtained during the planting process.

In an example, the vehicle for weed control management comprises an output unit. The output unit is configured to receive the crop seed map of the agricultural field and the soil surface profile map of the agricultural field from the control and processing unit. The output unit is configured to output the crop seed map of the agricultural field and the soil surface profile map of the agricultural field.

In other words, the crop seed map and the soil surface profile map can e.g. be shown to a farmer on a monitor, hand held, printer, screen or any other information monitoring device/medium.

According to a third aspect of the invention, there is provided a (second) vehicle for weed control management comprising at least one soil elevation sensor, a control and processing unit, and a transceiver. The at least one soil elevation sensor is configured to collect soil elevation data comprising elevations amounts and the corresponding geopositional information of the soil elevations on the agricultural field at a first time point. The at least one soil elevation sensor is configured to collect soil elevation data comprising elevations amounts and the corresponding geopositional information of the soil elevations on the agricultural field at a second time point which is after the first time point. The control and processing unit is configured to receive the soil elevation data from the at least one soil elevation sensor and to generate soil surface profile maps of the agricultural field at at least two different time points. The control and processing unit is configured to utilize the transceiver to receive a crop seed map of the agricultural field. The control and processing unit is configured to compare the soil surface profile maps and the crop seed map to identify differences in the soil elevation profile that are not associated with seed growth of the planted seeds on the agricultural field and to generate a weed control agent spray map.

To phrase it differently, a vehicle acquires soil elevation data at a first and a second time point (which can be e.g. a view days/weeks later than the first time point). The vehicle also receives information about the crop seed map as generated at an earlier point in time. The control and processing unit of the vehicle uses generated and received information to generate a weed control agent spray map. The calculation and generation of the crop seed map, the soil surface profile map(s) and/or the weed control agent spray map can also be done on an external processing unit and the information/analysis can be sent to the vehicle that requires the information/analysis.

In an example, the control and processing unit of the (second) vehicle is configured to utilize the transceiver to receive the soil elevation data comprising elevations amounts and the corresponding geopositional information of the soil elevations on the agricultural field at the first time point and/or the soil surface profile map of the agricultural field for the first time point.

In this manner, the second vehicle does only need to acquire soil elevation data at a second point in time and can use the soil elevation data as generated by a first vehicle (e.g. by a seed planter vehicle during the planting process) or other vehicles. The second vehicle for example receives the data via wireless communication and uses this information to generate a weed control agent spray map. Thus, it is possible that the second vehicle does generate the weed control agent spray map while being on the agricultural field which enables the vehicle to directly initiate weed control measurement while being at the location where weed control measurements are required.

In an example, the (second) vehicle for weed control management comprises an output unit. The output unit is configured to receive the weed control agent spray map for the agricultural field from the control and processing unit. The output unit is configured to output the weed control agent spray map for the agricultural field.

In an example, the (second) vehicle for weed control management comprises at least one weed control agent spray unit. The at least one weed control agent spray unit is configured to eject a weed control spray agent. The control and processing unit is configured to control the at least one weed control agent spray unit according to the weed control agent spray map.

Thus, the second vehicle which acquires the soil elevation data at a second time point has all data to generate the weed control agent spray map. In order to do so the vehicle can also use external processing capacity. However, at the same time when the vehicle is on the agricultural field acquiring soil elevation data for a second time point it can analyse the data and start with controlling the weeds e.g. by spraying an appropriate herbicidal product where required. This continuous process increases efficacy.

In a fourth aspect of the invention, there is provided a weed control agent spray map generated according to the method as discussed under the first aspect of the invention.

In a fifth aspect of the invention, there is provided a system for weed control management comprising a first vehicle for weed control management and a second vehicle for weed control management. The first vehicle comprises at least one seed position sensor, a control and processing unit, a seed planting unit, and a transceiver. The second vehicle comprises at least one soil elevation sensor, a control and processing unit, and a transceiver. The first vehicle is configured to plant crop seeds on an agricultural field with the seed planting unit. The at least one seed position sensor of the first vehicle is configured to collect seed geoposition data of the crop seeds impinging on the soil surface from the seed planting unit during planting. The control and processing unit of the first vehicle is configured to receive the seed position data of the at least one seed position sensor to generate a crop seed map of the agricultural field. The at least one soil elevation sensor from the second vehicle is configured to collect soil elevation data, the soil elevation data comprising elevations amounts and the corresponding geopositional information of the soil elevations on the agricultural field at a first time point and at a second time point which is later than the first time point. The control and processing unit of the second vehicle is configured to receive the soil elevation data from the at least one soil elevation sensor and to generate soil profile maps of the agricultural field at at least two different time points. The control and processing unit of the first vehicle is configured to utilize the transceiver to transmit the crop seed map of the agricultural field from to the second vehicle. The control and processing unit of the second vehicle is configured to utilize the transceiver to receive the crop seed map of the agricultural field from the first vehicle. The control and processing unit of the second vehicle is configured to compare the soil surface profile maps and the seed map to identify differences in the soil elevation profile that are not associated with seed growth of the planted seeds on the agricultural field and to generate a weed control agent spray map.

In an example, the system for weed control management comprises a first vehicle which further comprises at least one soil elevation sensor. The at least one soil elevation sensor of the first vehicle is configured to collect soil elevation data, the soil elevation data comprising elevations amounts and the corresponding geopositional information of the soil elevations on the agricultural field for the first time point. The control and processing unit of the first vehicle is configured to receive the soil elevation data from the at least one soil elevation sensor to generate a soil surface profile map of the agricultural field at a first time point. The control and processing unit of the first vehicle is configured to utilize the transceiver to transmit the soil surface profile map of the agricultural field at a first time point to the second vehicle. The control and processing unit of the second vehicle is configured to utilize the transceiver to receive the soil surface profile map of the agricultural field at a first time point from the first vehicle.

In an example, the system for weed control management comprises a second vehicle which further comprises at least one weed control agent spray unit. The at least one weed control agent spray unit is configured to eject a weed control spray agent. The control and processing unit of the second vehicle is configured to control the at least one weed control agent spray unit according to the weed control agent spray map.

According to another aspect, there is provided a computer program product, which when executed by a processor is configured to carry out the method of the first aspect.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
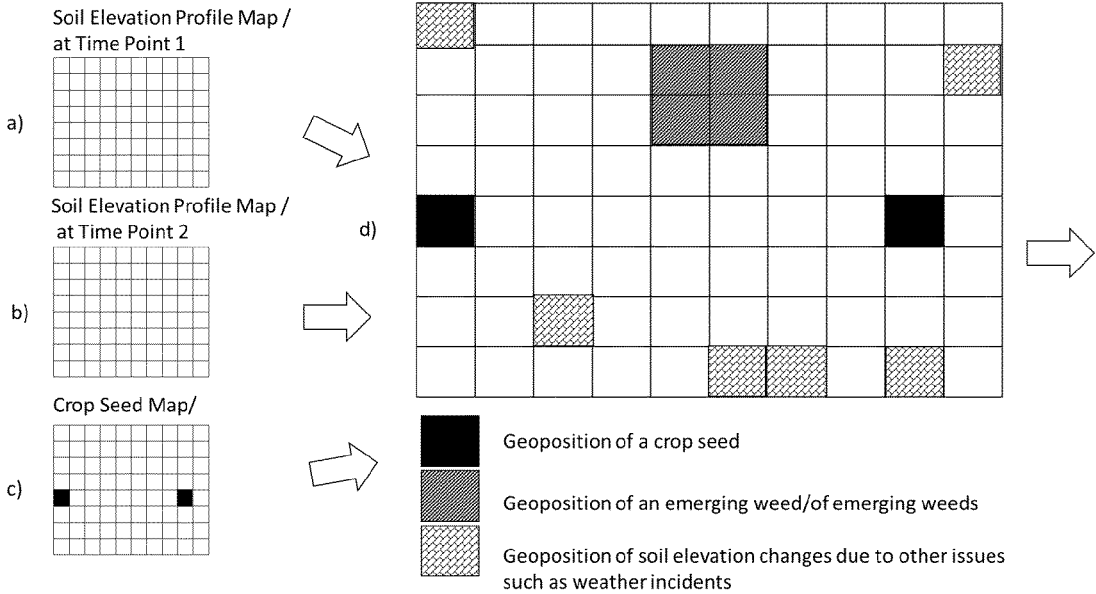
FIG. 1 shows a schematic example of the generation of a weed control agent spray map.
Figure 1:
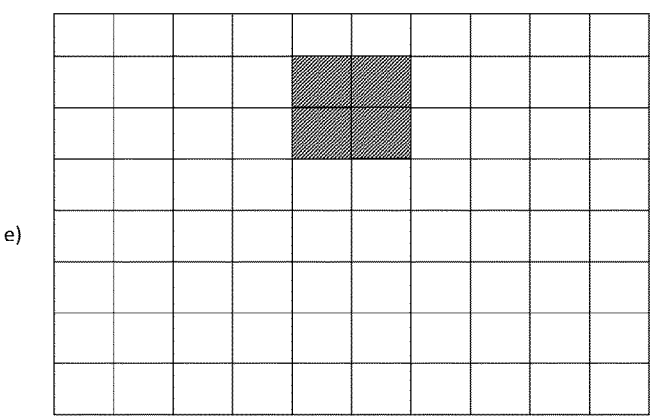

The invention relates in a first embodiment to a method 10 for weed control management. The method comprises the steps of:

a) acquiring geopositional information of planted crop seeds on an agricultural field and generating a crop seed map, b) acquiring soil elevation data and the corresponding geopositional information of the soil elevation on the agricultural field where the crop seeds have been planted or are being planted at at least two different time points and generating soil surface profile maps of the agricultural field, the soil surface profile maps showing the soil surface profiles at the at least two different time points, c) comparing the soil surface profile maps and the crop seed map to identify differences in the soil elevation profile that are not associated with seed growth of the planted seeds on the agricultural field, d) generating a weed control agent spray map on the basis of the differences in the identified soil elevations on the agricultural field that are not associated with seed growth of the planted crop seeds on the agricultural field.

In an example, the term "geopositional information" refers to the real-world geographic location e.g. as represented in geographic coordinates.

In an example, the terms "where the crop seeds have been planted or are being planted" refer to time points shortly after planting. E.g. when crops seeds have been planted with a vehicle with planting equipment on the front side of the vehicle and for which soil elevation data can be acquired in the same operational process with sensors at the rear side of the same vehicle. The time point can also be later e.g. a view days after planting. The data can also be acquired with a vehicle that is different to the seed planting vehicle.

In an example, the resolution of the geopositional information is ±10 cm, more preferably ±5 cm, and even more preferably ±2 cm, which can be obtained by a seed position sensor with a location determining means system such as a GPS-Real Time Kinetic (RTK) system.

In an example, information about the geopositional information of planted crop seeds on an agricultural field can be acquired with a camera, laser scanner, a one-dimensional line sensor for detecting seeds, a light beam, and a thermosensor for detecting heated-up seeds together with a position-determining system. US2014/0076216A1 discusses a method for precision drilling of seed grains and the registration of the seed position in a chart.

In an example, the crop seed map refers to the registration of the seed position in a chart particularly in the form of a at least two-dimensional (or alternatively three-dimensional) display of the crop seed geopositional distribution on an agricultural field after planting.

In an example, the soil elevation data and the corresponding geopositional information of the soil elevation on the agricultural field is acquired with a lidar sensor, a parallax laser rangefinder sensor, a stereo vision sensor, an IR reflectance sensor, a time of flight sensor, an ultrasonic sensor, a radar sensor.

In an example, a lidar sensor is used.

In an example, a 3D lidar sensor is used

In an example, a lidar sensor together with a camera is used. The camera can e.g. identify green parts of weeds that have already emerged and this information can be taken into account for the generation of the weed control agent spray map.

In an example, the camera is configured to operate over the visible wavelength range. In an example, the camera is configured to operate in the near infrared range. In an example, the camera is monochromatic. In an example, the camera is configured to acquire colour information such RGB. In an example, the camera is configured to acquire hyperspectral information.

In an example, a plurality of lidar scans at various locations across the agricultural field are acquired. This is done in order to provide a highly consistent lidar point density (number light detection and ranging measured points per unit area on a given target). One issue to consider for ground-based and/or close to the ground-based lidar sensoring is the potential unevenness of the point density over a scene where parts of the soil rendered closer to the scanner are more densely covered than the ones fare away. This can be addressed by various means such as for example by increasing the pulse repetition rate, changing the scan pattern, and/or the scan rate.

In an example, the soil elevation data and the corresponding geopositional information of the soil elevation on the agricultural field is acquired with a lidar sensor and with a position-determining system such as a GPS-Real Time Kinetic (RTK).

In an example, the at least two different time points refer to measurements of the soil elevation data and the corresponding geopositional information of the soil elevation at two different times with e.g. a time lag of e.g. a day, a week, 2 weeks, 3 weeks.

In an example, the soil elevation data is acquired on at a plurality of different time points and each compared to the previous soil elevation data. As an example, the soil elevation data is acquired on a daily basis.

In an example, a soil surface profile map refers a at least two-dimensional (or three-dimensional) display of the geopositional coordinates for the agricultural field, wherein for each geopositional coordinate the soil elevation amount is indicated (at the time of measurement). The data resolution of the geoposition (horizontal) is depending on the lidar and position determining means used and is preferably at least 2 cm, more preferably 1 cm and even more preferably below 1 cm. As concerns the measurement of soil elevation amount, todays lidar sensors have a resolution of a view millimeters to detect vertical differences which is sufficient to detect changes in the soil elevation profile indicating the germination and growth of weeds.

In an example, an algorithm is applied to correct for small geoposition shifts between two or more soil surface profile maps.

Figure 2:
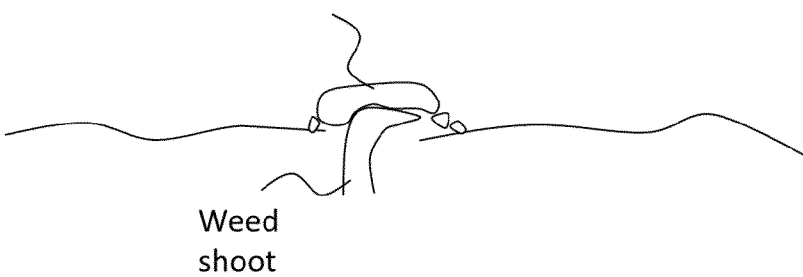
FIG. 2a) and b) show schematic examples of the weed germination process (from a side view perspective) and the soil elevation patterns generated by the weed germination process (from a top view perspective)
Figure 2:
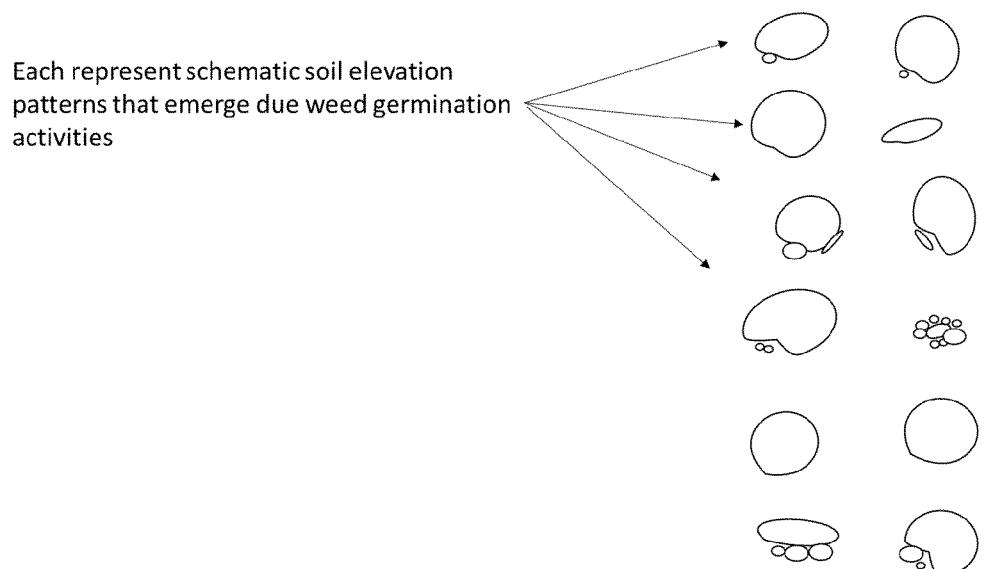

In an example, soil surface profile maps of at least two different time points are compared with each other (see FIG. 1, a, b). This comparison reveals changes in the soil elevation amounts for the same geoposition over time on the agricultural field (see FIG. 1, d). These differences can be further analysed with machine learning algorithms for patterns that relate to weed germination activities. When weeds germinate the shoot pushes against the soil above the shoot. The soil elevates above the shoot (see FIG. 2a, side view perspective). When analyzing these weed germination processes from above, patterns are revealed (see FIG. 2b of a schematic illustration of potential patterns from a top view perspective) which can be distinguished from other soil elevation changing incidences such e.g. for example weather activities. Also other soil elevation changes not due to germinating weeds can be analysed in a similar way and e.g. be classified with machine learning algorithms. By overlaying the crop seed map with the soil profile maps at at least two different time points (see FIG. 1 d) weeds that germinate can be identified and be distinguished from planted crop seeds and soil elevation changes that occurred due to other reasons such as weather incidences. Then, a weed control agent spray map can be generated (see FIG. 1 e). The weed control agent spray map is (at least) a two-dimensional (or three-dimensional) display of weed (germination and emergence) geopositional distribution on an agricultural field where a weed control agent can be applied to appropriately control the weeds on the field.

In an example, analysis of the soil elevation data/soil profile map comprises utilisation of a machine learning algorithm.

In an example, the machine learning algorithm comprises a decision tree algorithm.

In an example, the machine learning algorithm comprises an artificial neural network.

In an example, the machine learning algorithm has been taught on the basis of a plurality of soil elevation profile maps. In an example, the machine learning algorithm has been taught on the basis of a plurality of soil elevation profile maps containing soil elevation patterns due to at least one type of weed, various soil types and various soil moisture degrees. In an example, the machine learning algorithm has been taught on the basis of a plurality of soil elevation profile maps containing soil elevation patterns of a plurality of weeds, various soil types and various soil moisture degrees.

In an example, a machine learning algorithm similar as discussed above is used to identify weeds that have already emerged, the species of the weeds (at least monocotyledon/dicotyledon), growth stadium/size and geolocation.

In an example, data of weeds that have already emerged is used to generate the weed control spray map.

In an example, a radius of 20 cm, preferably 10 cm, more preferably 5 cm and even more preferably 3 cm around an individual crop seed is marked on the weed control agent spray map to be not sprayed with a weed control agent.

According to an example, the data for the crop seed map and the soil surface profile map showing the soil surface profile at the first time point are acquired on the agricultural field with an agricultural vehicle at the same time.

Figure 6:
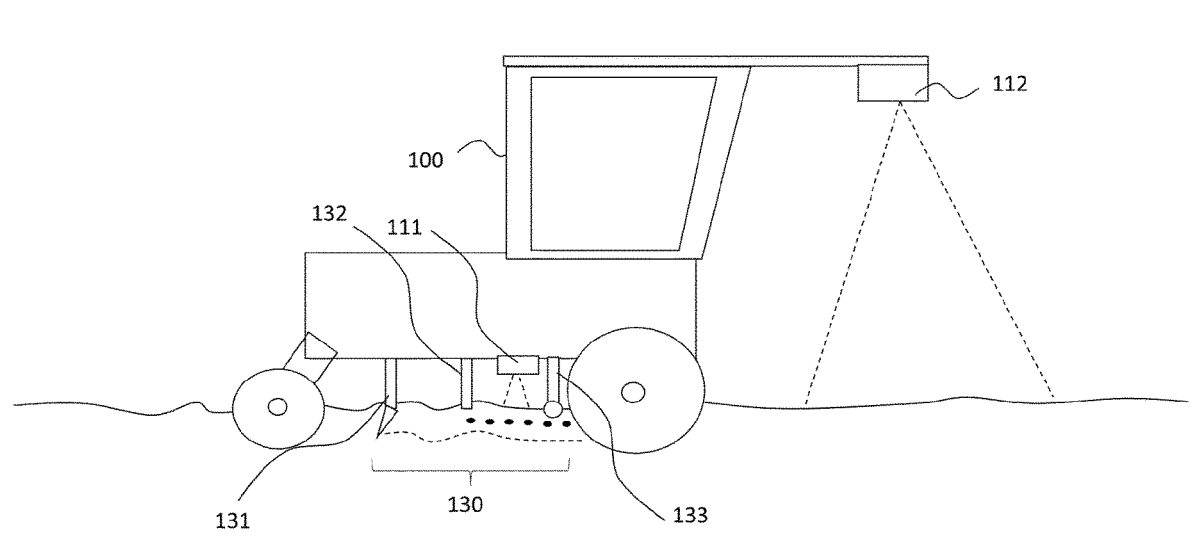
FIG. 6 shows a schematic set up of a detailed example of a vehicle (100) for weed control management (from a side view perspective)

In an example, the data for the crop seed map for a certain geolocation is acquired prior to the acquisition of the data for the soil surface profile at the first time point for the same geolocation (however, with the same vehicle). As an example FIG. 6 shows a vehicle, where the data for the crop seed map (e.g. a camera, see 111 in FIG. 6) for a certain location is acquired prior to the acquisition of the data for the soil surface profile at the first time point (see 112 in FIG. 6 and the moving direction of the vehicle 100) for the same location. In seed planting vehicles there is often a furrow closer 133 after the crop seeds have been put into the furrow which presses on the soil and closes the furrow. Therefore, it is necessary to acquire the data for the soil elevation after seed planting operations have been conducted.

In an example, the term "at the same time" refers to one continuous operation on the agricultural field with the same vehicle.

In an example, the "first time point" is shortly after the crop seeds have been planted.

According to an example, the method for weed control management further comprises step e) application of a weed control agent to the agricultural field according to the weed control agent spray map.

In an example, the weed control agent is a selective and/or a non-selective weed control agent. Thus, due to the precise weed control management method it is also possible to apply non-selective herbicides.

In an example, the weed control agent is a pre-emergence and/or an early post-emergence weed control agent.

According to an example, the method for weed control management the steps a) to e) are performed prior to the emergence and/or during the emergence of a plurality of shoots of the crop seeds and/or weeds on the agricultural field.

In an example, the method for weed control management is applied within the first two months, preferably within the first four weeks after planting of the crop seeds on the agricultural field.

According to an example, the method for weed control management acquires the geopositional information of the planted crop seeds on the agricultural field by at least one sensor that is configured to record geopositional information of the crop seeds impinging on the soil during planting of the crop seeds.

In an example, the at least one sensor that is configured to record geopositional information of the crop seeds impinging on the soil during planting of the crop seeds is selected from the group of a camera, laser scanner, a one-dimensional line sensor for detecting seeds, a light beam, and/or a thermosensor for detecting heated-up seeds; all together (and in synchronization) with a position determining means.

In an example, a location determining means comprise one or more of a GPS, an inertial navigation systems, or an image based location system. The GPS system is preferably a GPS-Real Time Kinetic (RTK) system. The location can be a geographical location, with respect to a precise location on the ground, or can be a location on the ground that is referenced to another position or positions on the ground, such as a boundary of an agricultural field. In other words, an absolute geographical location can be utilized or a location on the ground that need not be known in absolute terms, but that is referenced to a known location can be used.

In an example, the location is an absolute geographical location.

In an example, if a camera is used the location is a location that is determined with reference to a known location or locations. In other words, an image can be determined to be associated with a specific location on the ground, without knowing its precise geographical position, but by knowing the location where an image was acquired with respect to known position(s) on the ground the location where imagery was acquired can be logged. In other words, absolute GPS derived locations of where a vehicle has acquired imagery of the ground could be provided, and/or the locations of where imagery was acquired relative to a known position such as a field boundary could be provided, which again enables the control and processing unit to determine the exact positions where imagery was acquired because they would know the absolute position of the field boundary.

In an example, a GPS unit is used to determine, and/or is used in determining, the location, such as e.g. the location of the camera when specific images were acquired.

In an example, an inertial navigation unit is used alone, or in combination with a GPS unit, to determine the location, such as e.g. the location of the camera when specific images were acquired.

According to an example, the method for weed control management acquires the soil elevation data and the corresponding geopositional information of the soil elevation on the agricultural field is acquired with a sensor that is configured to generate pulses of light towards the soil surface and to measure the time for any reflections together (and in synchronization) with location determining means.

In an example, the sensor that is configured is configured to generate pulses of light towards the soil surface and to measure the time for any reflections is selected from the group of a lidar sensor, a parallax laser rangefinder sensor, a stereo vision sensor, an IR reflectance sensor, a time of flight sensor, an ultrasonic sensor, a radar sensor.

In an example, a lidar sensor is used.

In an example, a 3D lidar sensor is used.

In an example, a lidar sensor together with a camera is used. The camera can e.g. identify green parts of weeds that have already emerged, and this information can be taken into account for the generation of the weed control agent spray map.

In an example, the lidar sensor and/or the camera can acquire data/images of the soil close to the nadir (straight downwards) for optimum resolution.

In an example, the lidar sensor and/or the camera can acquire data/images of the soil closer to the horizontal plane (approximately 20-40° from the horizontal).

In an example, data/images of the same geoposition on the agricultural field are acquired from different angles such as close to the nadir and approximately 20-40° from the horizontal. For weeds that have already emerged dicotyledon plants imaging close to the nadir would be most effective while for monocotyledon plants imaging closer to the horizontal plane would be most effective.

In an example, the location determining means comprise one or more of a GPS, an inertial navigation systems, or an image based location system (similarly as described above the in the context of the crop seed position sensor). It is also possible that a plurality of sensors use together one location determining means to synchronise geopositional information to each individual sensor data.

Figure 3:
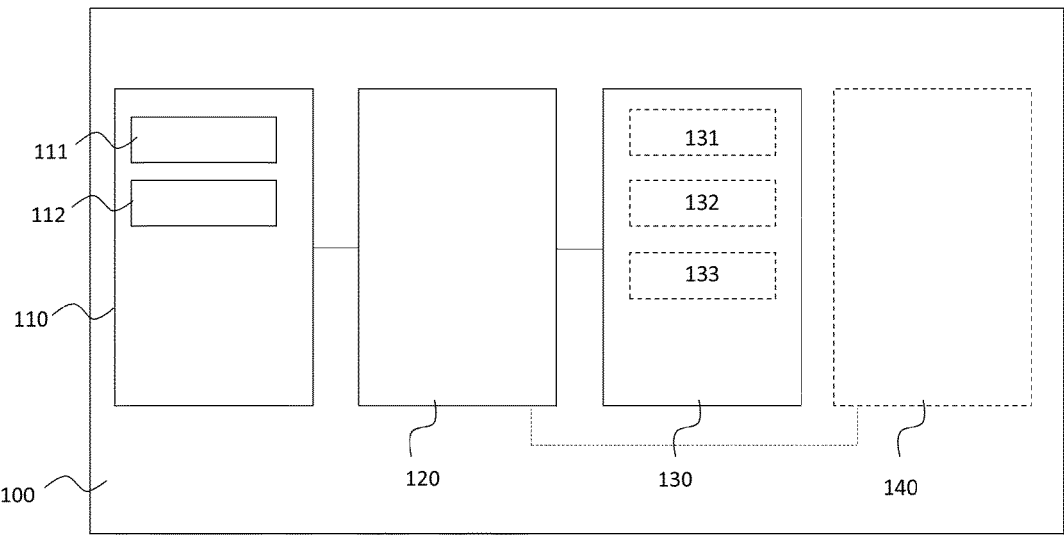
FIG. 3 shows a schematic set up of an example of a vehicle (100) for weed control management.

FIG. 3 shows a schematic example of a vehicle 100 for weed control management. The vehicle 100 for weed control management comprises a plurality of sensors 110 comprising at least one seed position sensor 111 and at least one soil elevation sensor 112; a control and processing unit 120, and a seed planting unit 130. The vehicle 100 is configured to plant crop seeds on an agricultural field with the seed planting unit 130. The at least one seed position sensor 111 is configured to collect seed geoposition data of the crop seeds impinging on the soil surface from the seed planting unit 130 during planting. The control and processing unit 120 is configured to receive the seed geoposition data from the at least one seed position sensor 111 to generate a crop seed map of the agricultural field. The at least one soil elevation sensor 112 of the vehicle is configured to collect soil elevation data, the soil elevation data comprising elevations amounts and the corresponding geopositional information of the soil elevations on the agricultural field. The control and processing unit 120 is configured to receive the soil elevation data from the at least one soil elevation sensor 112 to generate a soil surface profile map of the agricultural field, wherein the soil surface profile map shows the soil surface profile at a first time point. The seed position data and the soil elevation data are acquired at the same instance when the plant crop seeds are planted on an agricultural field with the seed planting unit of the vehicle.

In an example, the vehicle 100 is an Unmanned Ground Vehicle (UGV), a tractor, a seed planter vehicle, an Unmanned Aerial Vehicle (UAV), preferably an UGV, tractor or seed planter vehicle.

In an example, the at least one seed position sensor 111 is (as described above for the method) preferably selected from the group of a camera, laser scanner, a one-dimensional line sensor for detecting seeds, a light beam, and/or a thermosensor for detecting heated-up seeds; all together with a position determining means. Appropriate position determining means are discussed in context with the method.

In an example, the at least one soil elevation sensor 112 is (as described above for the method) preferably selected from the group of a lidar sensor, a parallax laser rangefinder sensor, a stereo vision sensor, an IR reflectance sensor, a time of flight sensor, an ultrasonic sensor, a radar sensor.

In an example, a lidar sensor is used.

In an example a 3D lidar sensor is used

In an example, a lidar sensor together with a camera is used.

In an example, the control and processing unit 120 can completely be part of the vehicle or can have external at least on addition external processing unit and the control and processing unit 120 communicates via wireless data transmission with the external processing unit (which can be an external computer, cloud etc.).

In an example, the seed planting unit 130 comprises at least one seed dosing system 132 configured to deposit the crop seed onto the soil.

In an example, the seed planting unit 130 further comprises at least one furrow opener 131 configured to open a furrow in the soil.

In an example, the seed planting unit 130 further comprises at least one furrow closer 133 configured to close the furrow.

In an example, the furrow closer 133 is a wheel.

In an example, the seed is deposited by the seed dosing system 132 into the furrow as generated by the at least one furrow opener 131.

In an example the seed planting unit 130 and the at least one seed position sensor 111 are attached to/positioned closer to the front of the vehicle in comparison to the at least one soil elevation sensor 112 which is attached to/positioned closer to the rear side of the vehicle and preferably behind the back wheels of the vehicle.

According to an example, the vehicle 100 for weed control management further comprises: an output unit 140. The output unit 140 is configured to receive the crop seed map of the agricultural field and the soil surface profile map of the agricultural field from the control and processing unit 120. The output unit 140 is configured to output the crop seed map of the agricultural field and the soil surface profile map of the agricultural field.

In an example, the output unit comprises a monitor, a printer, a screen, an information monitoring device and/or any other information monitoring medium.

Figure 4:
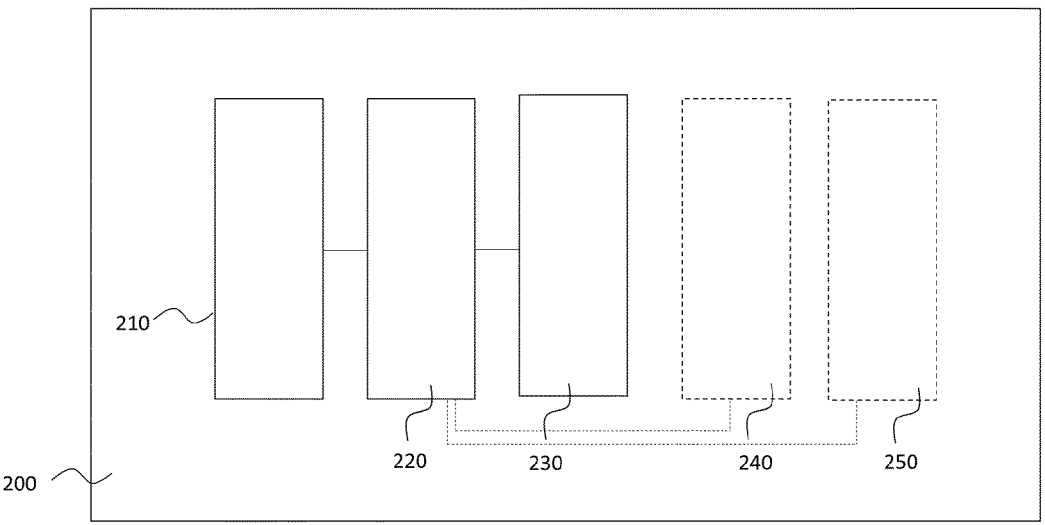
FIG. 4 shows a schematic set up of an example of a vehicle (200) for weed control management.

FIG. 4 shows a schematic example of a vehicle 200 for weed control management. The vehicle 200 for weed control management comprises at least one soil elevation sensor 210, a control and processing unit 220, and a transceiver 230. The at least one soil elevation sensor 210 is configured to collect soil elevation data comprising elevations amounts and the corresponding geopositional information of the soil elevations on the agricultural field at a first time point. The at least one soil elevation sensor 210 is configured to collect soil elevation data comprising elevations amounts and the corresponding geopositional information of the soil elevations on the agricultural field at a second time point which is after the first time point. The control and processing unit 220 is configured to receive the soil elevation data from the at least one soil elevation sensor 210 and to generate soil surface profile maps of the agricultural field at at least two different time points. The control and processing unit 220 is configured to utilize the transceiver 230 to receive a crop seed map of the agricultural field. The control and processing unit 220 is configured to compare the soil surface profile maps and the crop seed map to identify differences in the soil elevation profile that are not associated with seed growth of the planted seeds on the agricultural field and to generate a weed control agent spray map.

In an example, the vehicle 200 is an Unmanned Ground Vehicle (UGV), a tractor, an Unmanned Aerial Vehicle (UAV), preferably an UAV or tractor.

In an example, the at least one soil elevation sensor 210 is a similar sensor as the one described in the context of the at least one soil elevation sensor 112.

In an example, the crop seed map of the agricultural field has been generated by the first vehicle 100. This information about the crop seed map is transmitted to the second vehicle 200 (e.g. from the first vehicle directly to the second vehicle or via data cloud or an external processing unit preferably via wireless communication).

According to an example, the vehicle 200 for weed control management comprises a control and processing unit 220 configured to utilize the transceiver 230 to receive the soil elevation data comprising elevations amounts and the corresponding geopositional information of the soil elevations on the agricultural field at the first time point and/or the soil surface profile map of the agricultural field for the first time point.

In an example, the second vehicle 200 acquires soil elevation data comprising elevations amounts and the corresponding geopositional information of the soil elevations on the agricultural field at a second time point (and not for the first time point). Similarly as with the crop seed map, the second vehicle 200 receives the soil elevation data and/or the soil surface profile map for the first time point from the first vehicle 100 (or another vehicle) directly or via data cloud or an external processing unit. When the second vehicle 200 comprises a weed control agent spray unit 250 it is possible that the vehicle acquires the soil elevation data for the second time point, receives all other data required to generate the weed control agent spray map with its transceiver, generated the weed control agent spray map and starts to control the weeds on the agricultural field with its weed control agent spray unit and this all in one operational procedure on the agricultural field.

According to another example, the vehicle 200 for weed control management comprises an output unit 240. The output unit 240 is configured to receive the weed control agent spray map for the agricultural field from the control and processing unit 220. The output unit 240 is configured to output the weed control agent spray map for the agricultural field.

In an example, the output unit 240 comprises a monitor, a printer, a screen, an information monitoring device and/or any other information monitoring medium. The output unit can also be another vehicle which receives the spray map in order to conduct the spraying operation.

In an example the vehicle 200 is an UAV and the information about the weed control agent spray map of the agricultural field is sent via wireless communication to an output unit.

According to another example, the vehicle 200 for weed control management comprises at least one weed control agent spray unit 250. The at least one weed control agent spray unit 250 is configured to eject a weed control spray agent. The control and processing unit 220 is configured to control the at least one weed control agent spray unit 250 according to the weed control agent spray map.

In an example, weed control spray unit 250 comprises at least one spray unit. The at least one spray unit is configured to spray a liquid.

In an example, a spray unit is e.g. a boom sprayer.

In an example, the term "control the at least one weed control agent spray unit" in the context of a spray unit refers to the control of the start of the spraying process and the control of the stop of the spraying process.

In an example, a spray unit comprises at least one liquid atomizer such as a hydraulic nozzle and/or at least one atomizing disc such as a spinning disc.

In an example, the at least one weed control agent spray unit comprises a, liquid atomizer, a liquid tank and at least one feed pipe. The liquid tank is configured to hold a liquid. The feed pipe is configured to transport the liquid from the liquid tank to the liquid atomizer. The liquid atomizer is configured to spray the liquid.

In an example, the term "liquid(s)" refer(s) to liquid(s) comprising chemical and/or biological based herbicidal active ingredients (such as a weed control agent as discussed herein before).

In an example, the control and processing unit is configured to control the at least one spray unit to apply the liquid either as a spray of fine droplets, a single jet, a single droplet, or a combination of these, depending on the preferred type of deposit.

According to another example, another embodiment of the invention relates to a weed control agent spray map generated according to the method of weed control management as described herein.

In an example, the weed control agent spray map is (at least) a two-dimensional (or three-dimensional) display of weed (germination and emergence) geopositional distribution on an agricultural field where a weed control agent can be applied to appropriately control the weeds on the field (see FIG. 1, *d*).

In an example, the information of the weed control agent spray map can be sent to a plurality of other vehicles (such as UAVs) which comprise spray units and are configured to apply herbicides according to the spray map at various locations on the agricultural field.

Figure 5:
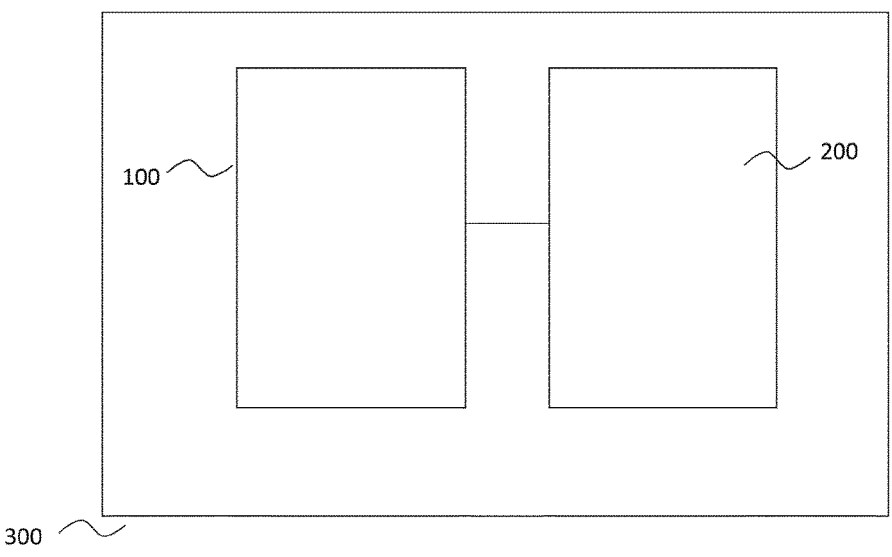
FIG. 5 shows a schematic set up of an example of a system (300) for weed control management.

FIG. 5 shows a schematic example of a system 300 for weed control management. The system 300 for weed control management comprising a first vehicle 100 for weed control management and a second vehicle 200 for weed control management. The first vehicle comprises at least one seed position sensor 111, a control and processing unit 120, a seed planting unit 130, and a transceiver 140. The second vehicle comprises at least one soil elevation sensor 210, a control and processing unit 220, and a transceiver 230. The first vehicle 100 is configured to plant crop seeds on an agricultural field with the seed planting unit 130. The at least one seed position sensor 111 of the first vehicle is configured to collect seed geoposition data of the crop seeds impinging on the soil surface from the seed planting unit 130 during planting. The control and processing unit 120 of the first vehicle is configured to receive the seed position data of the at least one seed position sensor 111 to generate a crop seed map of the agricultural field. The at least one soil elevation sensor 210 from the second vehicle 200 is configured to collect soil elevation data, the soil elevation data comprising elevations amounts and the corresponding geopositional information of the soil elevations on the agricultural field at a first time point and at a second time point which is later than the first time point. The control and processing unit 220 of the second vehicle 200 is configured to receive the soil elevation data from the at least one soil elevation sensor 210 and to generate soil profile maps of the agricultural field at at least two different time points. The control and processing unit 120 of the first vehicle is configured to utilize the transceiver 140 to transmit the crop seed map of the agricultural field from to the second vehicle 200. The control and processing unit 220 of the second vehicle 200 is configured to utilize the transceiver 230 to receive the crop seed map of the agricultural field from the first vehicle 100. The control and processing unit 220 of the second vehicle 200 is configured to compare the soil surface profile maps and the seed map to identify differences in the soil elevation profile that are not associated with seed growth of the planted seeds on the agricultural field and to generate a weed control agent spray map.

According to an example, the system 300 for weed control management comprises a first vehicle which comprises at least one soil elevation sensor 112. The at least one soil elevation sensor 112 of the first vehicle is configured to collect soil elevation data, the soil elevation data comprising elevations amounts and the corresponding geopositional information of the soil elevations on the agricultural field for the first time point. The control and processing unit 120 of the first vehicle is configured to receive the soil elevation data from the at least one soil elevation sensor 112 to generate a soil surface profile map of the agricultural field at a first time point. The control and processing unit 120 of the first vehicle is configured to utilize the transceiver 140 to transmit the soil surface profile map of the agricultural field at a first time point to the second vehicle 200. The control and processing unit 220 of the second vehicle 200 is configured to utilize the transceiver 230 to receive the soil surface profile map of the agricultural field at a first time point from the first vehicle 100.

In an example, the second vehicle 200 does not need to generate the soil surface profile map of the agricultural field at a first time point but receives this information from the first vehicle 100 or another vehicle.

According to an example, the system 300 for weed control management comprises a second vehicle 200 which comprises at least one weed control agent spray unit 250. The at least one weed control agent spray unit 250 is configured to eject a weed control spray agent. The control and processing unit 220 of the second vehicle 200 is configured to control the at least one weed control agent spray unit 250 according to the weed control agent spray map.

FIG. 6 shows a schematic set up of a detailed example of a vehicle 100 for weed control management. The vehicle shown is a ground vehicle such as a tractor and comprises a seed planting unit 130 with a furrow opener 132, a seed dosing system 132 and a furrow closer 133. The crop seed position sensor 111 is a camera which records the geoposition of the crop seeds in the soil. The camera is synchronised with a GPS system. The vehicle comprises a soil elevation sensor 112 such as a lidar scanner at the rear of the vehicle. Soil elevations are scanned with the lidar sensor (for the first time point) after the planting process with the planting unit 130 has been terminated.

Figure 7:
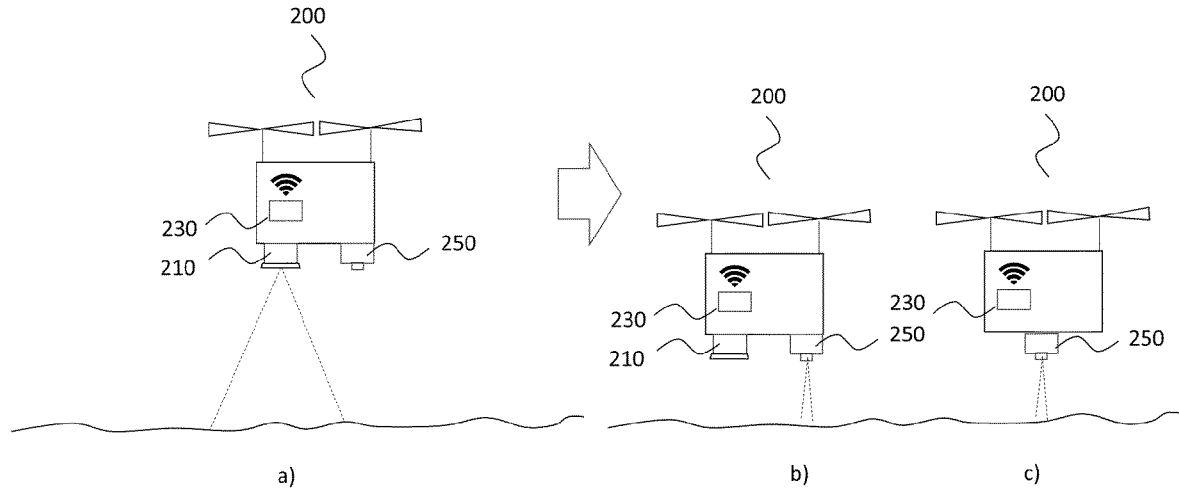
FIG. 7 shows a schematic set up of a detailed example of a vehicle (200) for weed control management (from a side view perspective)

FIG. 7 shows a schematic set up of a detailed example of a vehicle 200 for weed control management. The vehicle 200 in this example is an UAV. The UAV flies over an agricultural field and scans the ground beneath with a soil elevation sensor 210 such as a 3D lidar sensor (FIG. 7 *a*). A plurality of sensors on the UAV continuously record the position, altitude, height above the ground, and orientation of the lidar sensor to allow accurate position information to be included in the lidar image, which would be a detailed 3-D map of the soil surface. The UAV receives crop seed map data and soil elevation data for another earlier time point with the transceiver 230. The control and processing unit (not shown) uses the received information as well as the information from the soil elevation sensor 210 to assess where a herbicidal active ingredient needs to be applied to the soil (and therefore generates a spray map). Thus, comparison and analysis of two or more lidar images from the same agricultural field but acquired over a period of one or more days would show any differences from local changes in the height of the soil. The control and processing unit would analyse for changes indicative of growth underneath the soil surface from germinating seeds and catalogue the locations of these. An algorithm can be applied to correct for small geoposition shifts between two or more soil surface profile maps. The control and processing unit would also analyse growing plants, identify the species of plant, and if identified as an unwanted weed catalogue both the species, size and location of these. An algorithm can be applied to identify and eliminate false detections. The UAV 200 can also send its acquired soil elevation data to an external processing unit which does generate the spray map and send it back to the UAV 200 for spraying or another specialized spray UAV as shown in FIG. 7 *c*. FIG. 7 *b* indicates that the same UAV can use the spray map to directly control the weeds via its weed control unit 250. Alternatively, another UAV specialized to apply a weed control agent can receive the spray map from the UAV 200 and apply a weed control agent to the soil (see FIG. 7 *c*).

In another exemplary embodiment, a computer program or computer program product is provided that is characterized by being configured to execute the method steps of the method according to one of the preceding embodiments, on an appropriate system.

Figure 8:
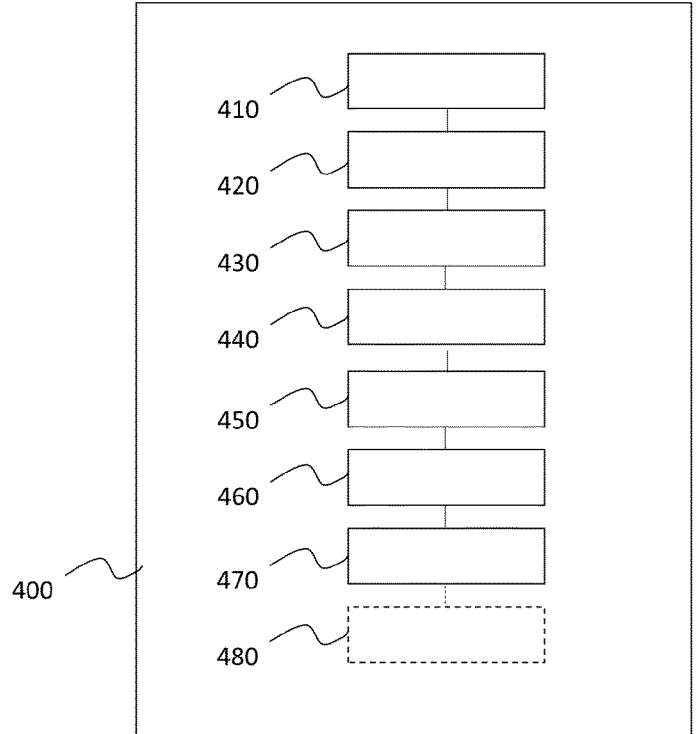
FIG. 8 shows a schematic set up of an example of a computer program product (400) for weed control management.

FIG. 8 shows a schematic set up of an example of a computer program product 400 for weed control management. The computer program product 400 for weed control management, which when executed by a processor is configured to carry out the steps of:

a) receiving 410 geopositional information of planted crop seeds on an agricultural field, b) generating 420 a crop seed map on the basis of the information received in step a), c) receiving 430 soil elevation data and the corresponding geopositional information of the soil elevation on the agricultural field where the crop seeds have been planted or are being planted at at least two different time points, d) generating 440 soil surface profile maps of the agricultural field, the soil surface profile maps showing the soil surface profiles at the at least two different time points on the basis of the information received in step c), e) comparing 450 the soil surface profile maps and the crop seed map, f) identifying 460 differences in the soil elevation profile that are not associated with seed growth of the planted seeds on the agricultural field, g) generating 470 a weed control agent spray map on the basis of the differences in the identified soil elevations on the agricultural field that are not associated with seed growth of the planted crop seeds on the agricultural field.

According to an example computer program product 400 for weed control management comprising the additional step:

e) instructing 480 a vehicle to apply a weed control agent to the agricultural field according to the weed control agent spray map.

The computer program product might be stored on a computer unit, which might also be part of an embodiment.

This computing unit may be configured to perform or induce performing of the steps of the method described above. Moreover, it may be configured to operate the components of the above described vehicle(s) and/or system. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses invention. Further on, the computer program product might be able to provide all necessary steps to fulfil the procedure of an exemplary embodiment of the method as described above.

According to a further exemplary embodiment of the present invention, a computer readable medium, such as a CD-ROM, USB stick or the like, is presented wherein the computer readable medium has a computer program product stored on it which is/can be a computer program product as described by the preceding section. A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network.

According to a further exemplary embodiment of the present invention, a medium for making a computer program product available for downloading is provided, which computer program product is arranged to perform a method according to one of the previously described embodiments of the invention.

It has to be noted that embodiments of the invention are described with reference to different subject matters. In particular, some embodiments are described with reference to method type claims whereas other embodiments are described with reference to the vehicle, spray map, and/or system type claims. However, a person skilled in the art will gather from the above and the following description that, unless otherwise notified, in addition to any combination of features belonging to one type of subject matter also any combination between features relating to different subject matters is considered to be disclosed with this application.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

What is claimed is:

1. A method to control weeds comprising the steps of:
   a) acquiring geopositional information of planted crop seeds on an agricultural field and generating a crop seed map;
   b) acquiring soil elevation data and the corresponding geopositional information of the soil elevation on the agricultural field where the crop seeds have been planted or are being planted at at least two different time points and generating soil surface profile maps of the agricultural field, the soil surface profile maps showing the soil surface profiles at the at least two different time points;
   c) comparing the soil surface profile maps and the crop seed map to identify differences in the soil elevation profile that are not associated with seed growth of the planted seeds on the agricultural field;
   d) generating a weed control agent spray map on the basis of the differences in the identified soil elevations on the agricultural field that are not associated with seed growth of the planted crop seeds on the agricultural field.

2. The method according to claim 1, wherein the data for the crop seed map and the soil surface profile map showing the soil surface profile at the first time point are acquired on the agricultural field with an agricultural vehicle at the same time.

3. The method according to claim 1, further comprising the step of:
   e) applying a weed control agent to the agricultural field according to the weed control agent spray map.

4. The method according to claim 3, wherein the steps a) to e) are performed prior to the emergence and/or during the emergence of a plurality of shoots of the crop seeds and/or weeds on the agricultural field.

5. The method according to claim 1, wherein the geopositional information of the planted crop seeds on the agricultural field is acquired by at least one sensor that is configured to record geopositional information of the crop seeds impinging on the soil during planting of the crop seeds.

6. The method according to claim 1, wherein the soil elevation data and the corresponding geopositional information of the soil elevation on the agricultural field is acquired with a sensor that is configured to generate pulses of light towards the soil surface and to measure the time for any reflections and location determining means.

7. A non-transitory computer-readable storage medium including executable instructions for weed control management, which when executed by at least one processor, cause the at least one processor to carry out the steps of:
   a) receiving geopositional information of planted crop seeds on an agricultural field;
   b) generating a crop seed map on the basis of the information received in step a);
   c) receiving soil elevation data and the corresponding geopositional information of the soil elevation on the agricultural field where the crop seeds have been planted or are being planted at at least two different time points;
   d) generating soil surface profile maps of the agricultural field, the soil surface profile maps showing the soil surface profiles at the at least two different time points on the basis of the information received in step c);
   e) comparing the soil surface profile maps and the crop seed map;

f) identifying differences in the soil elevation profile that are not associated with seed growth of the planted seeds on the agricultural field;

g) generating a weed control agent spray map on the basis of the differences in the identified soil elevations on the agricultural field that are not associated with seed growth of the planted crop seeds on the agricultural field.

8. The non-transitory computer-readable storage medium according to claim 7, wherein the executable instructions, when executed by the at least one processor, further cause the at least one processor to carry out the step of:

h) instructing a vehicle to apply a weed control agent to the agricultural field according to the weed control agent spray map.

* * * * *